(12) United States Patent
Adler et al.

(10) Patent No.: US 7,300,397 B2
(45) Date of Patent: Nov. 27, 2007

(54) ENDOSCOPE ELECTRONICS ASSEMBLY

(75) Inventors: Doron Adler, Nesher (IL); Ofer Pillar, Kiryat Haim (IL); Arie Blumenzweig, Netanya (IL); Shai Finkman, Haifa (IL); David Hanuka, Ramat Yishay (IL)

(73) Assignee: C2C Cure, Inc., Wilmington, DE (US)

( * ) Notice: Subject to any disclaimer, the term of this patent is extended or adjusted under 35 U.S.C. 154(b) by 549 days.

(21) Appl. No.: 10/901,376

(22) Filed: Jul. 29, 2004

(65) Prior Publication Data

US 2006/0025651 A1    Feb. 2, 2006

(51) Int. Cl.
*A61B 1/05* (2006.01)
(52) U.S. Cl. .................. 600/110; 600/920; 600/132
(58) Field of Classification Search ............... 600/109, 600/110, 112, 130, 132, 920; 348/75
See application file for complete search history.

(56) References Cited

U.S. PATENT DOCUMENTS

| | | |
|---|---|---|
| 3,971,065 A | 7/1976 | Bayer |
| 4,253,447 A | 3/1981 | Moore et al. |
| 4,261,344 A | 4/1981 | Moore et al. |
| 4,467,361 A | 8/1984 | Ohno et al. |
| 4,491,865 A | 1/1985 | Danna et al. |
| 4,555,768 A | 11/1985 | Lewis et al. |
| 4,569,335 A | 2/1986 | Tsuno |
| 4,576,146 A | 3/1986 | Kawazoe et al. |
| 4,604,992 A | 8/1986 | Sato |
| 4,643,170 A * | 2/1987 | Miyazaki et al. ........... 600/109 |

(Continued)

FOREIGN PATENT DOCUMENTS

EP    434793 B1    4/1995

(Continued)

OTHER PUBLICATIONS

Abstract of JP 4236934A, Jan. 1991.*

(Continued)

*Primary Examiner*—John P. Leubecker
(74) *Attorney, Agent, or Firm*—Ganz Law, P.C.

(57) ABSTRACT

A method for assembling an endoscope that includes an imaging subassembly inside an insertion tube having distal and proximal ends. The method includes coupling the imaging subassembly to a plurality of wires, which have respective first and second ends, by fixing the first ends of the wires to the imaging subassembly. A connector is coupled to the wires by fixing the second ends of the wires to the connector. After coupling the imaging subassembly and the connector to the wires, the imaging subassembly is installed in the insertion tube by passing the connector through the insertion tube from the distal end of the insertion tube to the proximal end. After passing the connector through the insertion tube, the connector is inserted in a receptacle.

8 Claims, 7 Drawing Sheets

U.S. PATENT DOCUMENTS

| | | | |
|---|---|---|---|
| 4,646,721 A | 3/1987 | Arakawa | |
| 4,651,201 A | 3/1987 | Schoolman | |
| 4,682,219 A | 7/1987 | Arakawa et al. | |
| 4,692,608 A | 9/1987 | Cooper et al. | |
| 4,697,208 A | 9/1987 | Eino | |
| 4,714,319 A | 12/1987 | Zeevi et al. | |
| 4,720,178 A | 1/1988 | Nishioka et al. | |
| 4,746,203 A | 5/1988 | Nishioka et al. | |
| 4,757,805 A | 7/1988 | Yabe | |
| 4,779,130 A * | 10/1988 | Yabe | 348/76 |
| 4,784,133 A | 11/1988 | Mackin | |
| 4,803,562 A | 2/1989 | Eino | |
| 4,809,680 A | 3/1989 | Yabe | |
| 4,819,065 A | 4/1989 | Eino | |
| 4,827,907 A | 5/1989 | Tashiro | |
| 4,832,003 A | 5/1989 | Yabe | |
| 4,857,724 A | 8/1989 | Snoeren | |
| 4,869,256 A | 9/1989 | Kanno et al. | |
| 4,871,229 A * | 10/1989 | Tashiro | 385/117 |
| 4,905,670 A | 3/1990 | Adair | |
| 4,926,257 A | 5/1990 | Miyazaki | |
| 4,934,339 A | 6/1990 | Kato | |
| 4,953,539 A | 9/1990 | Nakamura et al. | |
| 4,967,269 A | 10/1990 | Sasagawa et al. | |
| 4,986,642 A | 1/1991 | Yokota et al. | |
| 4,998,182 A * | 3/1991 | Krauter et al. | 361/730 |
| 4,998,972 A | 3/1991 | Chin et al. | |
| 5,010,875 A | 4/1991 | Kato | |
| 5,022,399 A | 6/1991 | Biegeleisen | |
| 5,029,574 A | 7/1991 | Shimamura et al. | |
| 5,122,650 A | 6/1992 | McKinley | |
| 5,166,787 A | 11/1992 | Irion | |
| 5,184,223 A | 2/1993 | Mihara | |
| 5,191,203 A | 3/1993 | McKinley | |
| 5,216,512 A | 6/1993 | Bruijns et al. | |
| 5,222,477 A | 6/1993 | Lia | |
| 5,311,600 A | 5/1994 | Aghajan et al. | |
| 5,323,233 A | 6/1994 | Yamagami et al. | |
| 5,325,847 A | 7/1994 | Matsuno | |
| 5,335,662 A | 8/1994 | Kimura et al. | |
| 5,343,254 A | 8/1994 | Wada et al. | |
| 5,376,960 A | 12/1994 | Wurster | |
| 5,432,543 A | 7/1995 | Hasegawa et al. | |
| 5,444,574 A | 8/1995 | Ono et al. | |
| 5,450,243 A | 9/1995 | Nishioka | |
| 5,471,237 A | 11/1995 | Shipp | |
| 5,494,483 A | 2/1996 | Adair | |
| 5,498,230 A | 3/1996 | Adair | |
| 5,512,940 A | 4/1996 | Takasugi et al. | |
| 5,547,455 A | 8/1996 | McKenna et al. | |
| 5,575,754 A | 11/1996 | Konomura | |
| 5,594,497 A | 1/1997 | Ahern et al. | |
| 5,598,205 A | 1/1997 | Nishioka | |
| 5,603,687 A | 2/1997 | Hori et al. | |
| 5,609,561 A * | 3/1997 | Uehara et al. | 600/112 |
| 5,653,677 A * | 8/1997 | Okada et al. | 600/112 |
| 5,673,147 A | 9/1997 | McKinley | |
| 5,700,236 A | 12/1997 | Sauer et al. | |
| 5,712,493 A | 1/1998 | Mori et al. | |
| 5,728,044 A | 3/1998 | Shan | |
| 5,751,341 A | 5/1998 | Chaleki et al. | |
| 5,792,045 A | 8/1998 | Adair | |
| 5,797,837 A | 8/1998 | Minami | |
| 5,879,285 A * | 3/1999 | Ishii | 600/110 |
| 5,905,597 A | 5/1999 | Mizouchi et al. | |
| 5,928,137 A | 7/1999 | Green | |
| 5,929,901 A | 7/1999 | Adair et al. | |
| 5,940,126 A | 8/1999 | Kimura | |
| 5,944,655 A | 8/1999 | Becker | |
| 5,984,860 A | 11/1999 | Shan | |
| 5,986,693 A | 11/1999 | Adair et al. | |
| 6,009,189 A | 12/1999 | Schaack | |
| 6,010,449 A | 1/2000 | Selmon et al. | |
| 6,019,719 A * | 2/2000 | Schulz et al. | 600/109 |
| 6,039,693 A | 3/2000 | Seward et al. | |
| 6,043,839 A | 3/2000 | Adair et al. | |
| 6,099,475 A | 8/2000 | Seward et al. | |
| 6,129,672 A | 10/2000 | Seward et al. | |
| 6,134,003 A | 10/2000 | Tearney et al. | |
| 6,139,490 A | 10/2000 | Breidenthal et al. | |
| 6,142,930 A | 11/2000 | Ito et al. | |
| 6,148,227 A | 11/2000 | Wagnieres et al. | |
| 6,178,346 B1 | 1/2001 | Amundson et al. | |
| 6,184,923 B1 | 2/2001 | Miyazaki | |
| 6,206,825 B1 | 3/2001 | Tsuyuki | |
| 6,281,506 B1 | 8/2001 | Fujita et al. | |
| 6,293,910 B1 * | 9/2001 | Yamakita et al. | 600/132 |
| 6,322,498 B1 * | 11/2001 | Gravenstein et al. | 600/120 |
| 6,331,156 B1 | 12/2001 | Haefele et al. | |
| 6,416,463 B1 | 7/2002 | Tsuzuki et al. | |
| 6,476,851 B1 | 11/2002 | Nakamura | |
| 6,485,414 B1 | 11/2002 | Neuberger | |
| 6,506,150 B1 * | 1/2003 | Ouchi | 600/132 |
| 6,533,722 B2 | 3/2003 | Nakashima | |
| 6,659,940 B2 | 12/2003 | Adler | |
| 6,670,636 B2 | 12/2003 | Hayashi et al. | |
| 6,692,430 B2 | 2/2004 | Adler | |
| 2001/0031912 A1 | 10/2001 | Adler | |
| 2001/0040211 A1 | 11/2001 | Nagaoka | |
| 2001/0051766 A1 | 12/2001 | Gazdzinski | |
| 2003/0174409 A1 | 9/2003 | Nagaoka | |
| 2004/0019255 A1 | 1/2004 | Sakiyama | |
| 2005/0259487 A1 | 11/2005 | Glukhovsky et al. | |
| 2005/0277808 A1 * | 12/2005 | Sonnenschein et al. | 600/112 |

FOREIGN PATENT DOCUMENTS

| | | |
|---|---|---|
| WO | WO9732534 A1 | 9/1997 |
| WO | WO99/23812 A2 | 11/1998 |
| WO | WO9960916 | 2/1999 |
| WO | WO/01/76452 | 10/2001 |
| WO | WO 03/098913 A3 | 11/2003 |

OTHER PUBLICATIONS

Abstract of JP 61018915A, Jul. 1984.*
Abstract of JP 60258515A, May 1985.*
Abstract of JP 06222283A2, Dec. 1993.*
Abstract of JP 63244011A, Mar. 1987.*
Abstract of JP 8024219A, Jan. 1996.*
Abstract of JP 08082751A, Mar. 1996.*
Abstract of JP 08114755A, May 1996.*
Abstract of JP 8220448A, Feb. 1995.*
Abstract of JP 7318815A, Jun. 1995.*
Abstract of JP 7163517A, Dec. 1993.*
Abstract of JP 08082751, Mar. 1996.*
Abstract of JP 2006198424, Mar. 2006.*
Abstract of JP 3264043A, Nov. 1991.*
Zebra® Elastomeric Connectors, available at: http://www/fujipoly.com/products/genProductLine.asp?ProductLine=Zebra, Nov. 2004, 3 pages.
http://www/fujipoly.com/general/default.asp, Nov. 2004, 2 pages.
United States Patent and Trademark Office Action dated Aug. 9, 2006 by Examiner Christopher L. Lavin for U.S. Appl. No. 10/759,045, filed Jan. 20, 2004, 9 pages.
European Examination Report for European Application No. 01919745.8, dated Jul.20, 2006, Primary Examiner V. Edward; EPO, 4 pages.
PCT International Search Report dated Oct. 21, 2001, for corresponding PCT International Application No. PCT/IL01/00313, filed Apr. 4, 2001, 3 pages.
PCT International Search Report dated Jul. 9, 2004, for corresponding PCT International Application No. PCT/US03/32975, filed Oct. 17, 2003.

PCT International Search Report dated Jun. 4, 2003, for corresponding PCT International Application No. PCT/IL02/00999, filed Dec. 11, 2002.

PCT International Search Report dated Mar. 24, 2004, for corresponding PCT International Application No. PCT/IL03/00399, filed May 15, 2003.

Fujipoly America Corp—Zebra Elastomeric Connectors, http://www.fujipoly.com/products/genProductLine.asp?Productline=zebra; accessed Jun. 11, 2004.

"A Review of the Optical Properties of Biological Tissues," Cheong, Prahl and Welch, IEEE Journal of Quantum Electronics, vol. 26, Dec. 12, 1990.

"Optical Properties of Circulating Human Blood in Wavelength Range 400-2500 nm," Andre Rosgan, Journal of Biomedical Optics, Jan. 1999.

* cited by examiner

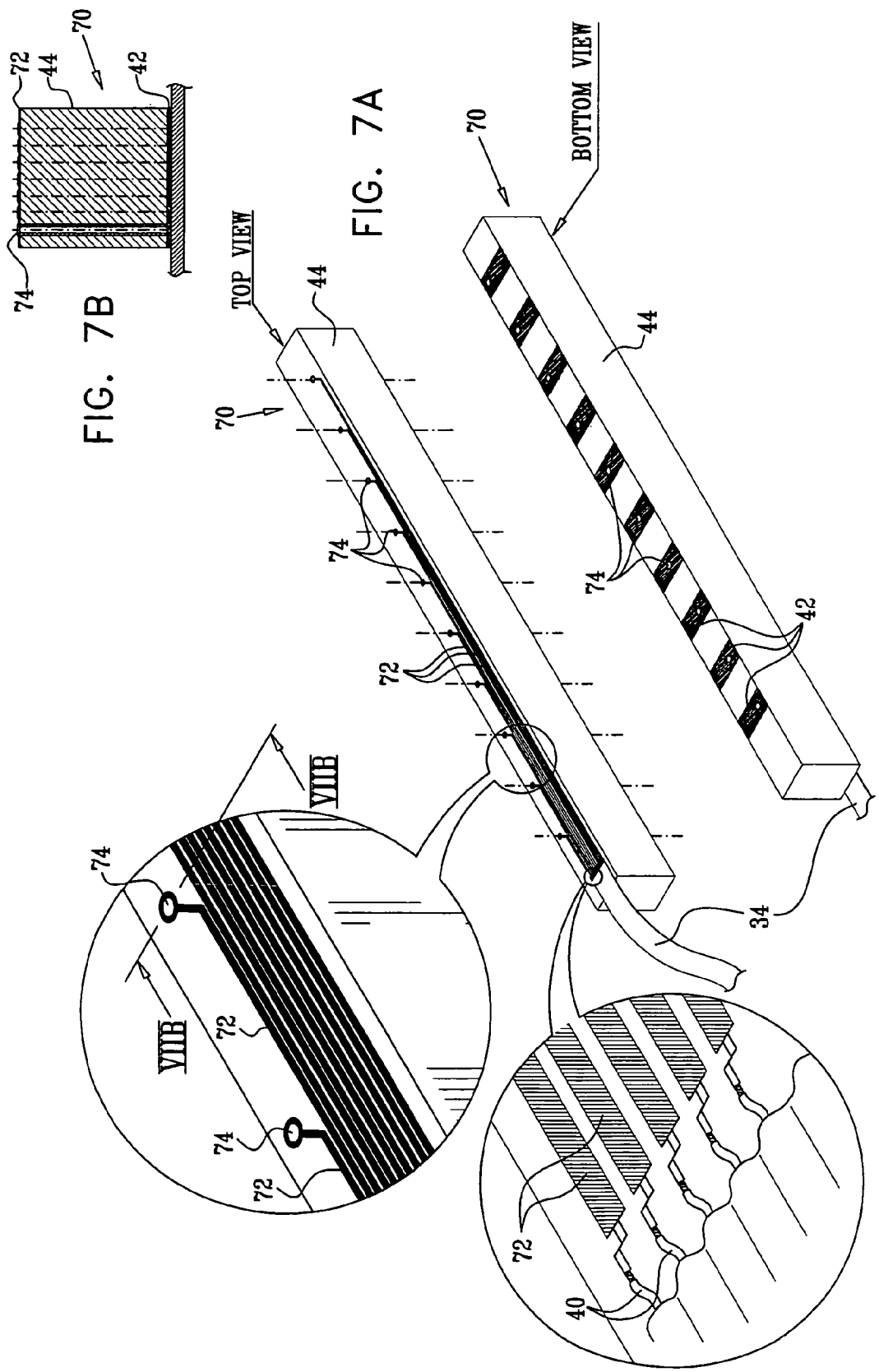

ENDOSCOPE ELECTRONICS ASSEMBLY

FIELD OF THE INVENTION

The present invention relates generally to endoscopy, and specifically to improved methods for assembly of endoscopes, as well as electronic parts and subassemblies for use in endoscopes.

BACKGROUND OF THE INVENTION

Electronic endoscopes typically comprise an imaging subassembly, comprising an image sensor and suitable optics, at the distal end of the endoscope insertion tube. The imaging subassembly is connected to wires that pass through the insertion tube to the proximal end of the endoscope, where they are connected to a video processor board. Typically, the video processor board provides power and control signals to the image sensor, and receives and processes raw video signals from the image sensor in order to generate standard video output.

Thus, in general, the electronics assembly of the endoscope (comprising the imaging subassembly, video processor board and connecting wires) can undergo final testing only after the entire endoscope has been assembled, whereupon the wires are connected to the imaging assembly at one end of the insertion tube and the video processor board at the other. If a fault in the electronics assembly is discovered at this late stage, it may be necessary to disassemble the entire endoscope in order to repair it.

SUMMARY OF THE INVENTION

There is a need for new methods of assembling endoscopes that permit the electronics assembly to be completely assembled and tested before it is assembled into the endoscope. Embodiments of the present invention that are described hereinbelow provide methods and devices that address this need.

In these embodiments, the electronics assembly comprises an imaging subassembly, wires, and a long, narrow connector, which is thin enough to pass through the endoscope insertion tube. The imaging subassembly is fixed to the distal end of the wires, and the connector is fixed to the proximal end, by soldering or by any other suitable technique, before the wires are passed through the insertion tube. The electronics assembly may then be tested by plugging the connector into a suitable video processor board or test jig. After testing, the electronics assembly is installed in the insertion tube by passing the connector through the insertion tube from the distal end of the insertion tube to the proximal end. After the connector and wires have passed through the insertion tube, the imaging subassembly is installed and sealed in the distal end of the insertion tube. The connector may then be plugged into a suitable receptacle in a processing subassembly, and the endoscope is ready for use.

Although the embodiments described hereinbelow relate specifically to imaging subassemblies, the principles of the present invention are equally applicable to other types of electronic subassemblies that are installed at the distal end of an endoscope and must be connected to processing or control electronics at the proximal end. Furthermore, the novel connectors and methods of assembly described hereinbelow may be used not only in endoscopes, but also in other types of electronic devices and systems.

There is therefore provided, in accordance with an embodiment of the present invention, a method for assembling an endoscope that includes an imaging subassembly inside an insertion tube having distal and proximal ends, the method including:

coupling the imaging subassembly to a plurality of wires, which have respective first and second ends, by fixing the first ends of the wires to the imaging subassembly;

coupling a connector to the wires by fixing the second ends of the wires to the connector;

after coupling the imaging subassembly and the connector to the wires, installing the imaging subassembly in the insertion tube by passing the connector through the insertion tube from the distal end of the insertion tube to the proximal end; and after passing the connector through the insertion tube, inserting the connector in a receptacle.

In a disclosed embodiment, the method includes testing the imaging subassembly by receiving signals from the connector after coupling the imaging subassembly and the connector to the wires and before installing the imaging subassembly in the insertion tube.

Typically, inserting the connector in the receptacle includes coupling the imaging subassembly to convey signals to a processing subassembly via the wires.

In some embodiments, the connector has an axis and includes a first array of conductive elements disposed along the axis, and coupling the connector to the wires includes connecting the wires to the conductive elements. Typically, the receptacle includes a second array of conductive pads, and coupling the connector to the receptacle includes aligning the first and second arrays, and exerting a pressure on at least one of the connector and the receptacle so as to engender an electrical contact between the conductive elements and the conductive pads. In a disclosed embodiment, coupling the connector to the receptacle includes inserting between the first and second arrays an elastomeric material including alternating conductive and non-conductive layers so that the electrical contact is formed through the elastomeric material.

Additionally or alternatively, the connector includes a dielectric substrate, and the conductive elements are formed from a layer of conductive material that is disposed on the dielectric substrate. Further additionally or alternatively, while passing the connector through the insertion tube, the axis of the connector is approximately parallel to the wires.

There is also provided, in accordance with an embodiment of the present invention, an electronic assembly for use in an endoscope that includes an insertion tube, the assembly including:

an imaging subassembly, including an image sensor;

an elongate connector, which has an axis and includes a first array of conductive elements disposed along the axis, and which has transverse dimensions that are sufficiently small to permit the connector to pass through the insertion tube of the endoscope; and wires, which have respective first ends that are fixed to the imaging subassembly and respective second ends that are fixed to the connector so as to electrically couple the imaging subassembly to the conductive elements of the connector.

There is additionally provided, in accordance with an embodiment of the present invention, a connector assembly, including:

an elongate connector, which has an axis and includes a first array of conductive elements disposed along the axis, and which is adapted for coupling of respective wires to the conductive elements;

a receptacle, of a size and shape suitable for receiving the connector, and including a second array of conductive pads, positioned so as to be aligned with the first array when the connector is inserted in the receptacle; and an elastomeric material, which includes alternating conductive and non-conductive layers, and which is adapted to be held in the receptacle between the first and second arrays so as to provide electrical contact between the conductive elements and the conductive pads when the connector is inserted in the receptacle.

In disclosed embodiments, the connector includes a dielectric substrate, and the conductive elements are formed from a layer of conductive material that is disposed on the dielectric substrate. Typically, the layer of conductive material is disposed on at least first and second sides of the substrate, wherein the first side is configured to contact the elastomeric material, and wherein the wires are attached to the conductive material on the second side. In one embodiment, the first and second sides are opposing sides of the substrate, and wherein the conductive material on the second side is electrically connected by through-holes passing through the substrate to the conductive elements on the first side.

There is further provided, in accordance with an embodiment of the present invention, an endoscope, including:

an insertion tube having distal and proximal ends and having an internal dimension;

an electronic assembly, which is installed inside the insertion tube, and includes:

an imaging subassembly, including an image sensor, positioned in the distal end of the insertion tube;

an elongate connector, which protrudes from the proximal end of the insertion tube, and which has transverse dimensions that are smaller than the internal dimension of the insertion tube; and wires, which pass through the insertion tube and which have respective first ends that are fixed to the imaging subassembly and respective second ends that are fixed to the connector so as to electrically couple the imaging subassembly to the connector; and a processing assembly, including a receptacle that is adapted to receive the connector outside the proximal end of the insertion tube.

The present invention will be more fully understood from the following detailed description of the embodiments thereof, taken together with the drawings in which:

BRIEF DESCRIPTION OF THE DRAWINGS

FIGS. 3A and 3C are schematic bottom and top views of a connector, while

FIG. 7A is a schematic, pictorial view of a connector, in accordance with another embodiment of the present invention; and FIG. 7B is a schematic, sectional view of the connector shown in FIG. 7A, taken along the line VIIB-VIIB.

DETAILED DESCRIPTION OF EMBODIMENTS

Figure 1:
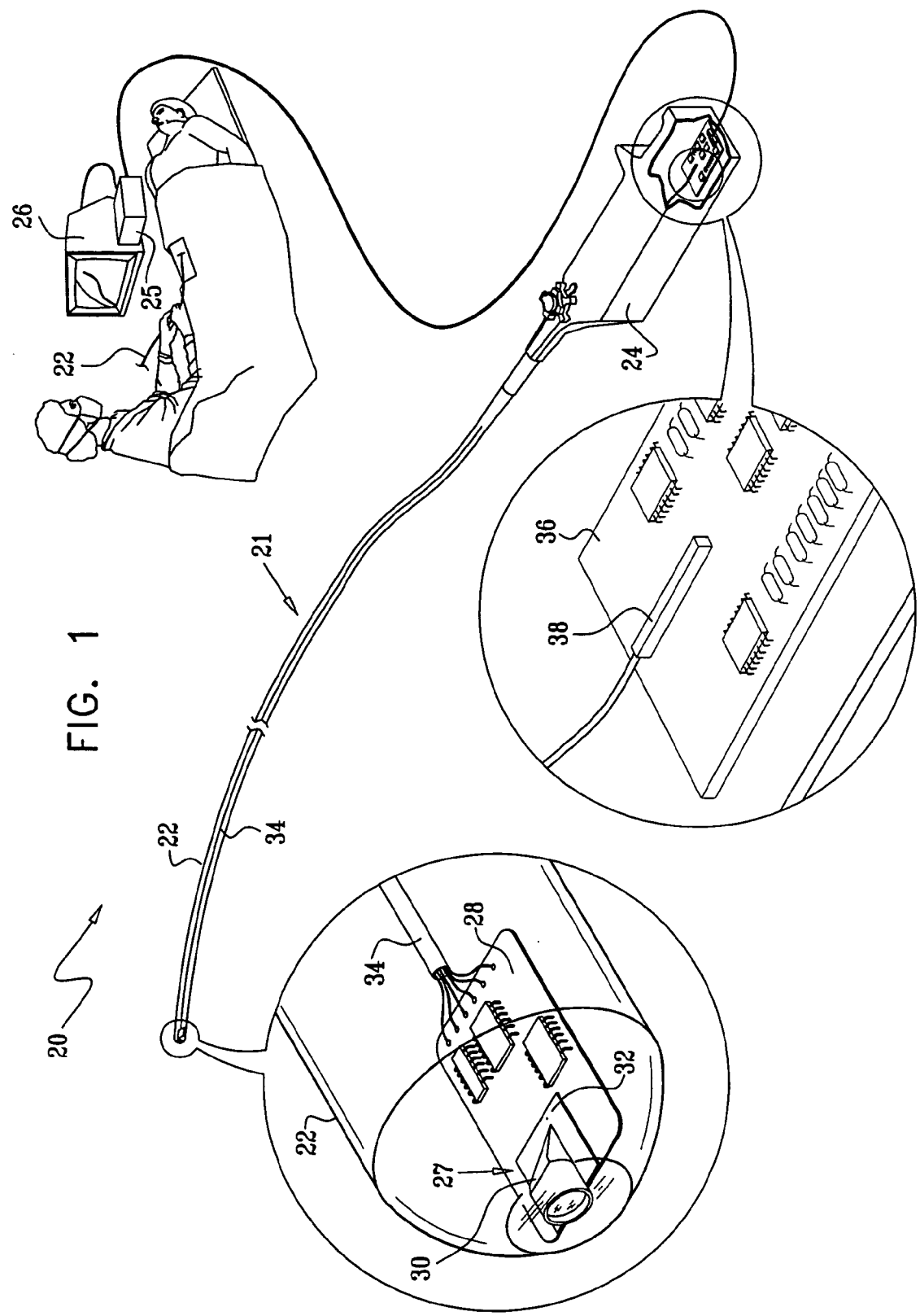
FIG. 1 is a schematic, cutaway view of a system for endoscopy, in accordance with an embodiment of the present invention.

FIG. 1 is a schematic, cutaway view of a system 20 for endoscopy, in accordance with an embodiment of the present invention. System 20 comprises an electronic endoscope 21, comprising an insertion tube 22 and a handle 24, which is coupled by cable to a control unit 25. An imaging subassembly 27 is installed in the distal end of the insertion tube, and is coupled by a cable 34 running through the insertion tube to a proximal processing subassembly, which in this embodiment comprises an interface board 38 in handle 24. The imaging subassembly captures images of a region outside the distal end of the insertion tube (typically images of the inside of a body cavity or passageway). The image signals are passed from board 38 to control unit 25, which processes the images for display on a display monitor 26.

Imaging subassembly 27 comprises a circuit board 28, typically a printed circuit board, which may be rigid or flexible, or may have both rigid and flexible parts. An image sensor 32, such as a CCD or CMOS sensor array, is mounted on board 28, along with ancillary electronic components. Objective optics 30 form an image of the region outside the distal end of insertion tube 22 on sensor 32. In the embodiment shown in FIG. 1, sensor 32 is oriented in a plane that is parallel to the longitudinal axis of insertion tube 22, and optics 30 comprise a prism for reflecting the images onto the sensor plane. Typically, endoscope 22 also comprises a light source, for illuminating the region outside the distal end, as well as other functional elements, which are omitted from the figures for the sake of simplicity. Further details of an endoscope of this sort are described in PCT publication WO 03/098913, whose disclosure is incorporated herein by reference. This particular configuration is shown here solely by way of example, however, and the principles of the present invention are equally applicable to endoscopes having different image sensor configurations, including endoscopes in which the sensor plane is perpendicular to the axis of the insertion tube.

Image sensor 32 generates raw video signals (which may be analog or digital signals) responsively to the light that is imaged onto the sensor elements by optics 30. The signals are carried through tube 22 by cable 34. The proximal end of cable 34 terminates in a novel connector 36, which mates with a suitable receptacle on a interface board 38. Typically, board 38 also supplies power and control signals through cable 34 to board 28. The connector and receptacle are described in detail hereinbelow.

Figure 2:
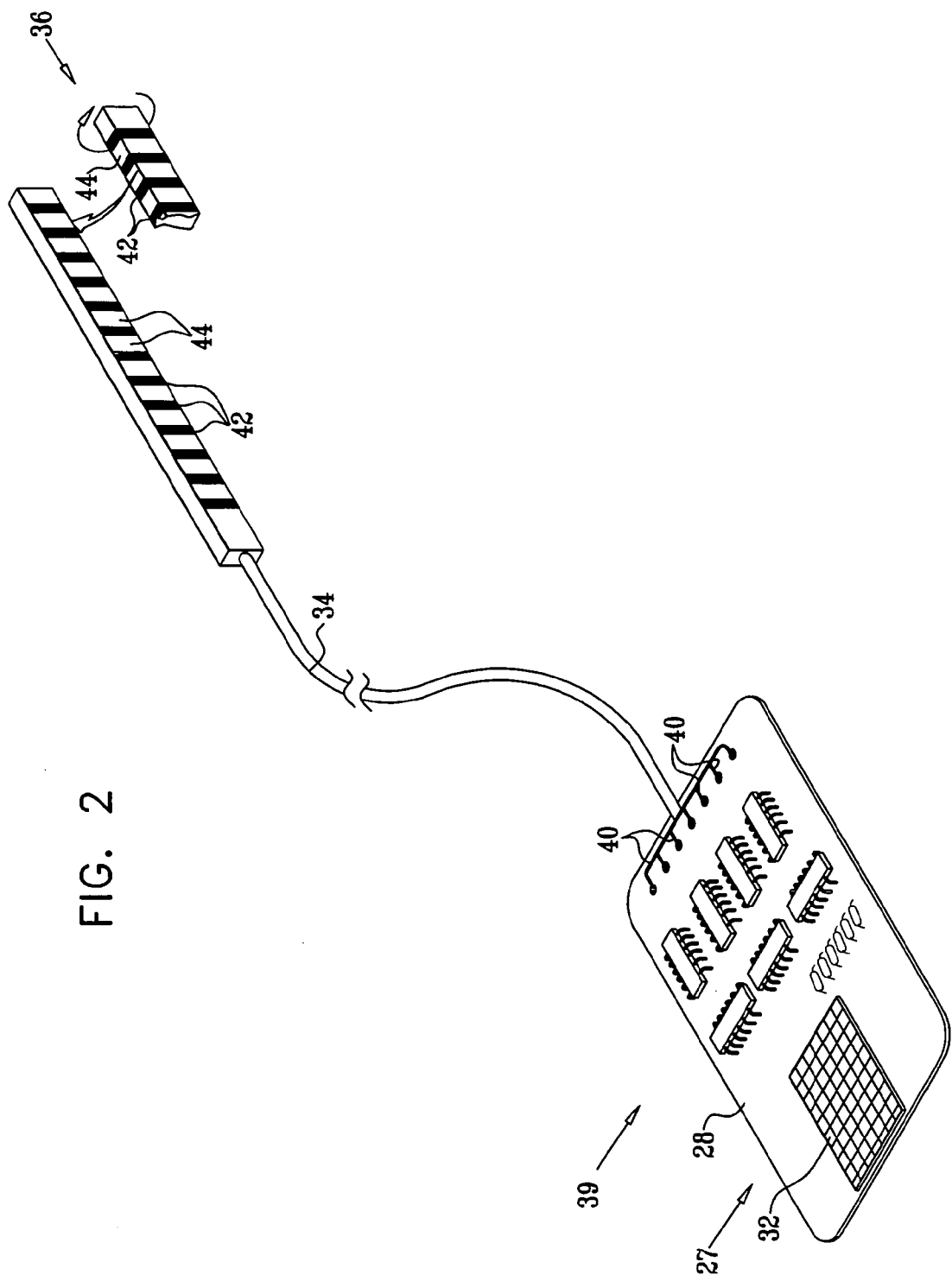
FIG. 2 is a schematic, pictorial view of an electronics assembly for use in an endoscope, in accordance with an embodiment of the present invention.

FIG. 2 is a schematic, pictorial view of an electronics assembly 39 used in system 20, in accordance with an embodiment of the present invention. Assembly 39 comprises imaging subassembly 27, cable 34 and connector 36. The imaging subassembly includes board 28, image sensor 32, and possibly optics 30, as well (not shown in this figure), which may be fixed to the image sensor. Cable 34 comprises multiple wires 40, whose distal ends are soldered to corresponding pads on board 28. Alternatively, the wires may be fixed to subassembly 27 by other means, as are known in the art.

Connector 36 comprises an array of conductive elements 42 on a non-conducting substrate 44. In other words, the connector comprises alternating conducting and non-conducting segments, arrayed along the longitudinal axis of the connector. Further details of connector 36 are shown in FIGS. 3A-D. Each of wires 40 is fixed at its proximal end to one of elements 42, thus providing a connection between board 28 and the connector elements.

Figure 3A:
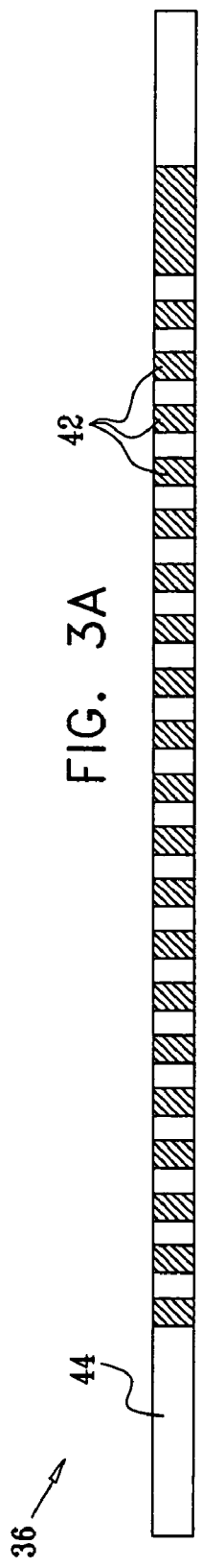
Figure 3B:
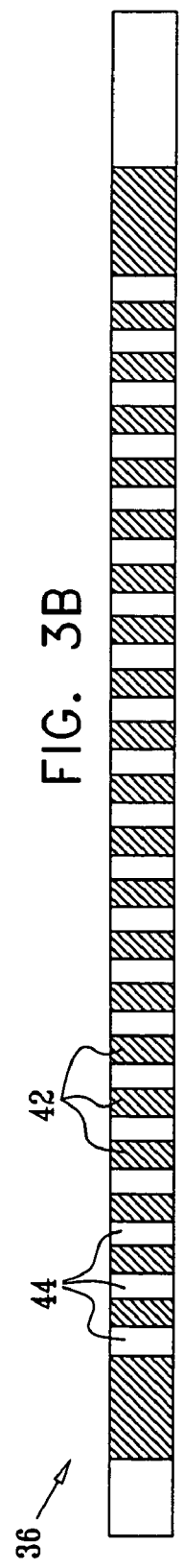
FIGS. 3B and 3D are schematic left and right side views of the connector, in accordance with an embodiment of the present invention.
Figure 3C:
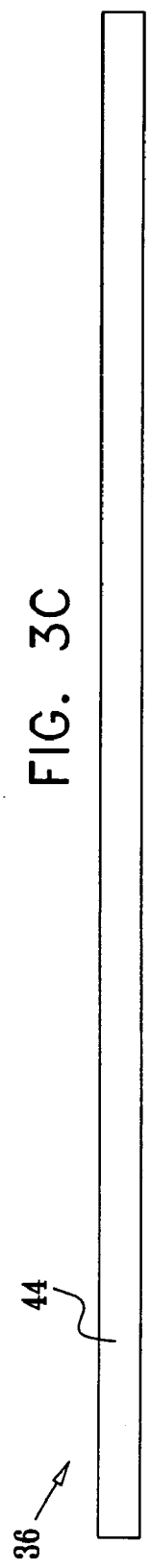
Figure 3D:
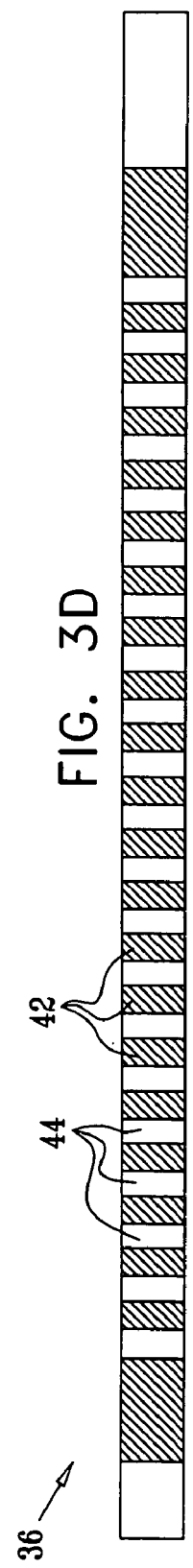

FIGS. 3A-D are schematic frontal views showing the four surfaces of connector 36, in accordance with an embodiment of the present invention. FIG. 3A shows the bottom surface of the connector, which contacts the receptacle on board 38. FIG. 3C is the opposite, top surface, and FIGS. 3B and 3D are the two sides of the connector. In this embodiment, substrate 44 of connector 36 comprises a glass-epoxy printed circuit substrate, which is approximately 0.6 mm wide, 1.2 mm high and 29 mm long. The transverse dimensions, perpendicular to the longitudinal axis of the connector, are sufficiently small so that the connector can pass through insertion tube 22 even after wires 40 have been attached to conductive elements 42. The conductive elements are about 0.5 mm wide, and have a center-to-center pitch of about 1 mm. Conductive elements 42 typically comprise copper with a tin/lead coating, and are formed as a layer on substrate 44 using a printed circuit production process. As shown in FIGS. 3A, 3B and 3D, the copper is plated around three sides of the substrate.

Wires 40 are fixed to connector 36 by soldering the wires to elements 42, so that each wire contacts one element. Typically, for ease of assembly, the wires are soldered to alternating sides the connector, so that some of the wires are soldered to the side shown in FIG. 3B, and the remaining wires to the side shown in FIG. 3D. After soldering the wires, the sides of the connector are potted in an insulating, protective coating, such as an epoxy coating, while leaving the top and bottom of the connector bare. Alternatively, other materials and methods known in the art may be used to fabricate connector 36, and other methods may be used to connect the wires to the conductive elements of the connector. The dimensions given above are listed solely by way of example, and can be made larger or smaller to accommodate application needs and production constraints.

Figure 4:
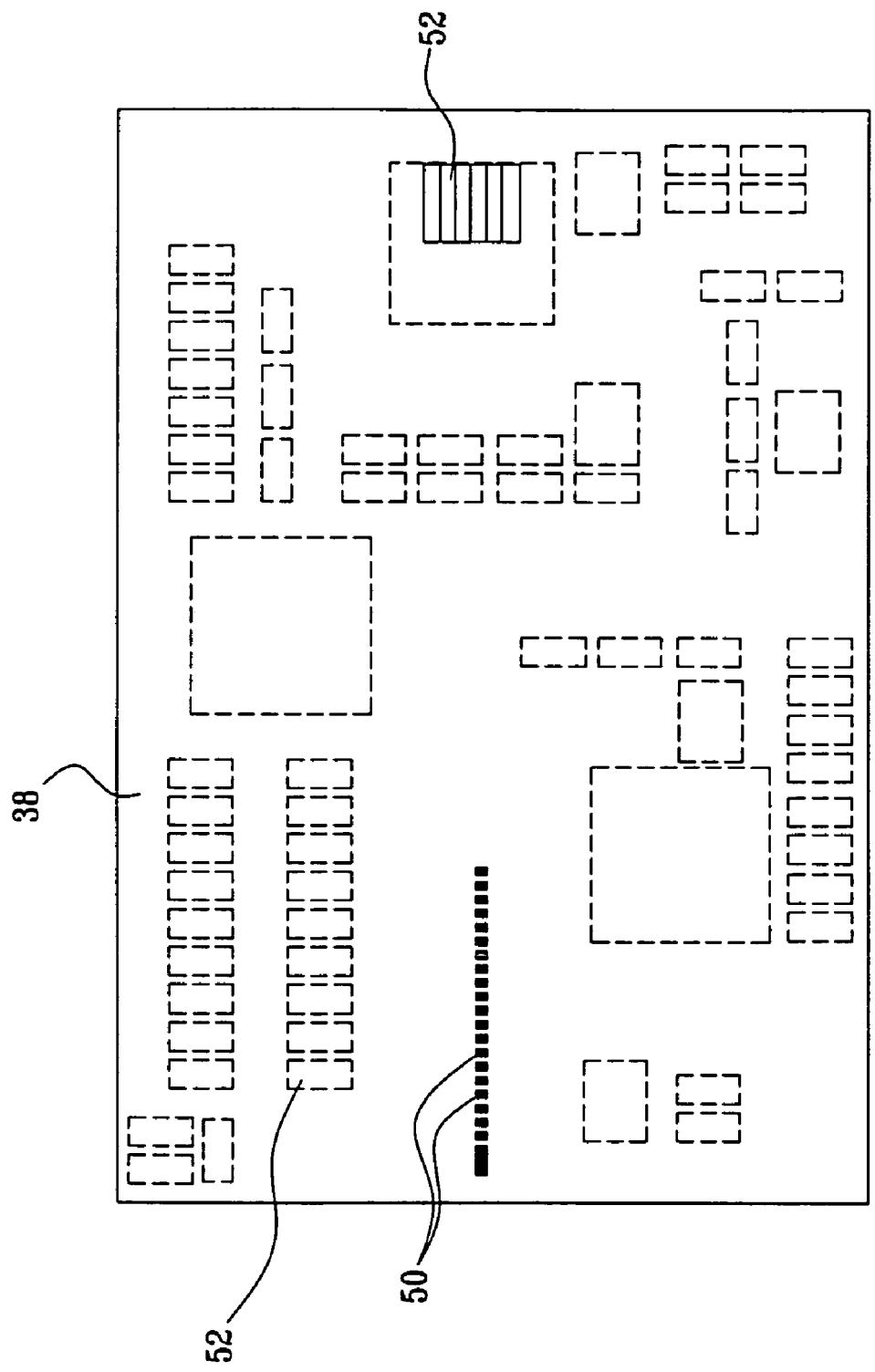
FIG. 4 is a schematic top view of a processing board for use with the assembly of FIG. 2, in accordance with an embodiment of the present invention.

FIG. 4 is a schematic top view of interface board 38, in accordance with an embodiment of the present invention. Board 38 is a printed circuit board, which comprises an array of conductive pads 50 having the same pitch as conductive elements 42. Pads 50 are connected to circuit elements on board 38 by traces on the reverse side of the board (not shown). A connector 52 at the other side of board 38 is used to connect the board to in the cable leading to control unit 25.

Figure 5A:
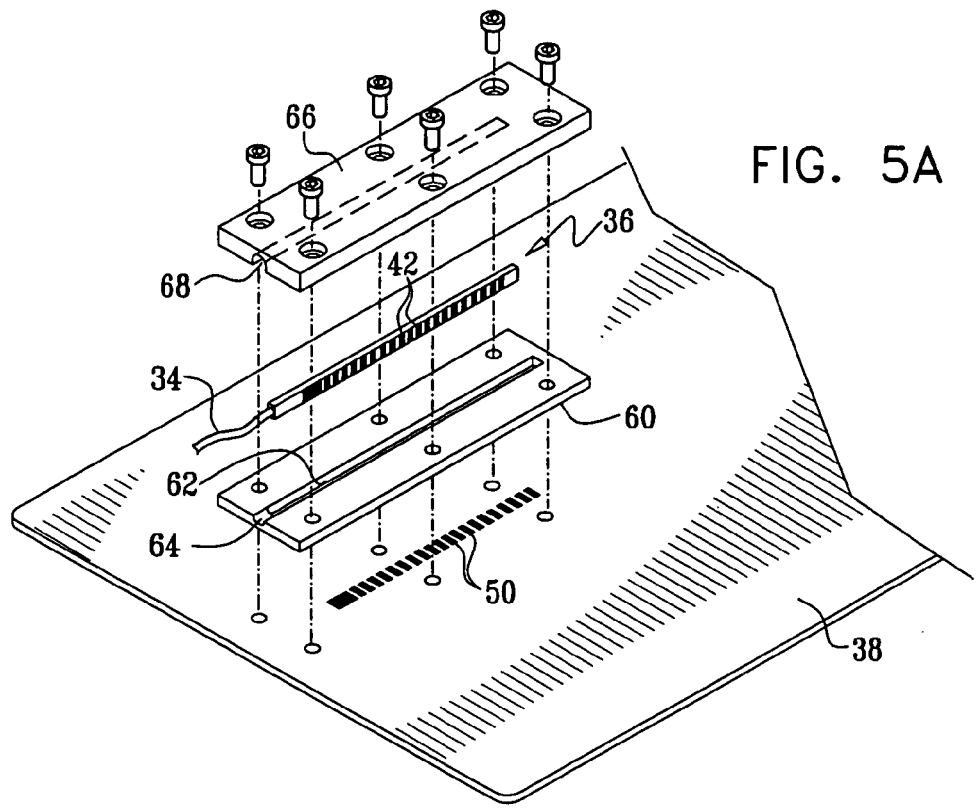
FIG. 5A is a schematic, exploded view of a connector, processing board, and receptacle for coupling the connector to the processing board, in accordance with an embodiment of the present invention.
Figure 5B:
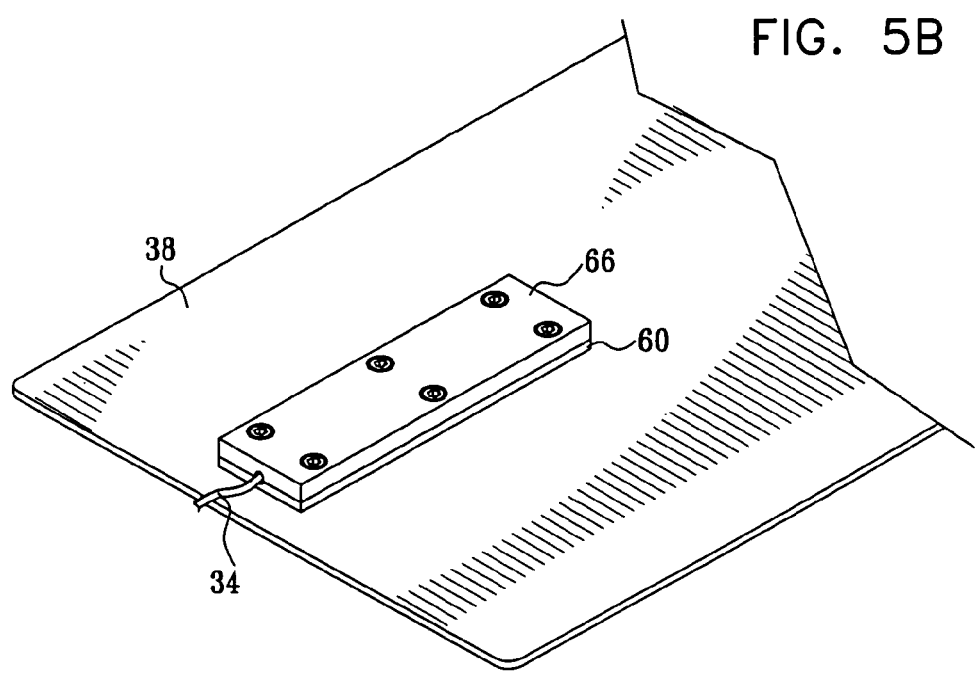
FIG. 5B is a schematic, pictorial illustration of the connector, board and receptacle of FIG. 5A after completion of the connection between the connector and the board.

Reference is now made to FIGS. 5A and 5B, which schematically illustrate how connector 36 is brought into electrical contact with board 38, in accordance with an embodiment of the present invention. FIG. 5A is an exploded view of the parts involved, while FIG. 5B shows the parts following completion of the assembly. A receptacle 60 is fixed to board 38 over the array of pads 50, so that a slot 64 in the receptacle is longitudinally aligned with the axis of the array. A piece of conductive elastomeric material 62 is inserted into slot 64. For example, material 62 may comprise a ZEBRA® elastomeric connector, distributed by Fujipoly America Corporation (Carteret, N.J.). The ZEBRA connector is constructed of alternating parallel layers of electrically conductive and nonconductive silicone elastomer. The ZEBRA material is oriented so that the alternating layers are perpendicular to the axis of the array.

Connector 36 is positioned over slot 64 above elastomeric material 62, so that each conductive element 42 is aligned with a corresponding pad 50 on board 38. A cover 66, with a slot 68 for holding the connector, is mechanically fastened to receptacle 60 so as to clamp connector 36 against material 62. Due to the pressure now exerted by connector 36 against material 62, the alternating conductive layers of the elastomeric material provide a reliable electrical connection between each element 42 and its corresponding pad 50. This arrangement has the advantage that it permits connector 36 to be made very thin, with no protruding connector pins, and that it enables connection and disconnection between connector 36 and board 38 to be made with essentially no insertion or removal force.

In other embodiments of the present invention, different designs may be used for connector 36, and different methods may be used for coupling the connector to board 38. Other connector types may be used in this context as long as the connectors are narrow enough to fit through insertion tube 22, as described with reference to the figure that follows.

Figure 6:
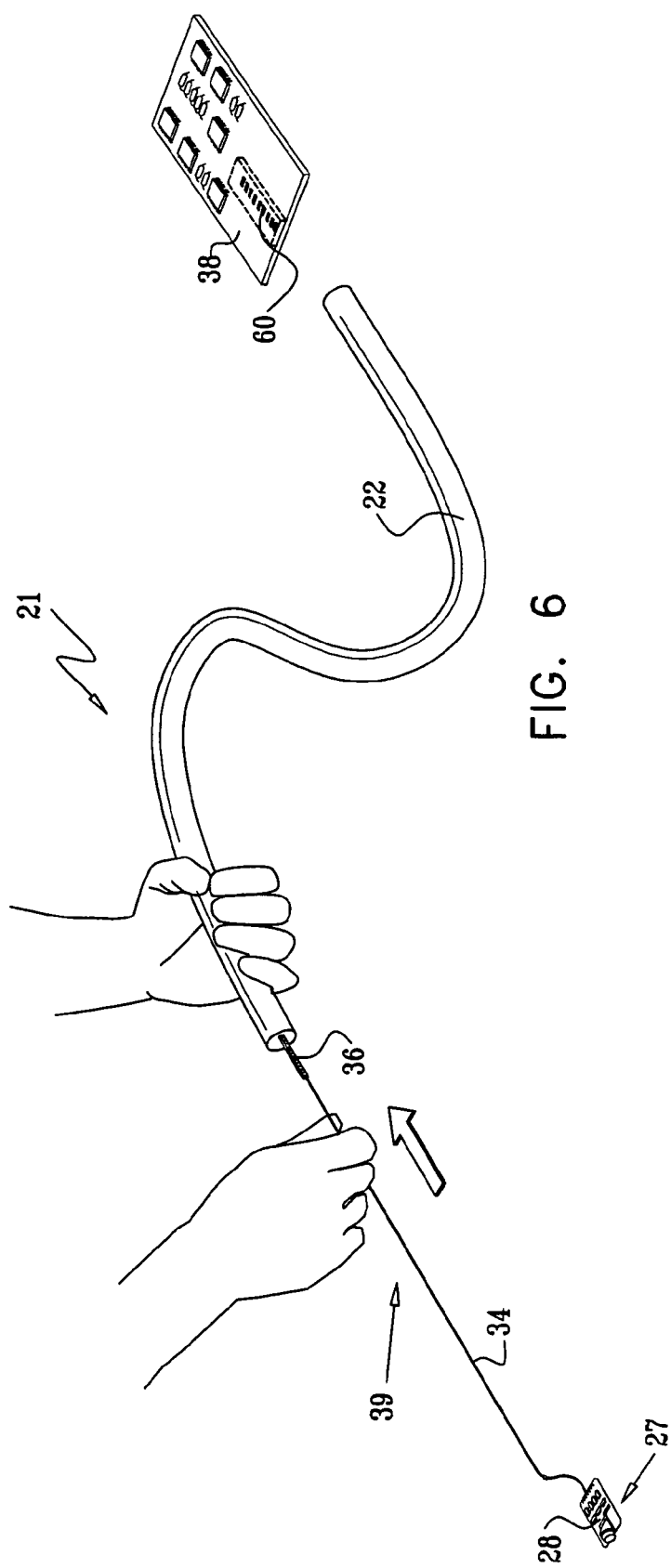
FIG. 6 is a schematic, pictorial illustration of an endoscope, showing a method for installation of an electronics assembly in the insertion tube of the endoscope, in accordance with an embodiment of the present invention.

FIG. 6 is a schematic, pictorial illustration of endoscope 21 showing installation of electronics assembly 39 in insertion tube 22, in accordance with an embodiment of the present invention. Assembly 39 is first assembled outside insertion tube 22, by soldering together (or otherwise connecting) board 28, cable 34 and connector 36, and installing the components of imaging subassembly 27 on board 28. Assembly 39 may then be tested, either by plugging connector 36 into the actual processing board 38, or by plugging the connector into a suitable test jig (with a receptacle similar to that shown in FIG. 5). This arrangement permits complete electrical and functional testing of assembly 39 to be completed while the assembly is outside insertion tube 22. As a result, defective parts can be identified and repaired or replaced before assembly 39 is installed in the endoscope. Because of the zero-force nature of the connection between connector 36 and the mating receptacle, there is little or no risk of damage to the connector due to repeated connect and disconnect operations that may occur during testing.

After testing is completed, connector 36 is inserted into the distal end of insertion tube 22, with the long axis of the connector parallel to the tube and to cable 34. The connector is passed through tube 22 to the proximal end, pulling cable 34 along behind it. When the connector has been passed all the way through the insertion tube, imaging subassembly is installed in the distal end of the tube, and the distal end is sealed. At this point, connector 36 protrudes from the proximal end of the tube. The connector may then be connected to board 38 in the manner described above.

FIGS. 7A and 7B schematically illustrate a connector 70, which may be used in place of connector 36 in accordance with an alternative embodiment of the present invention. FIG. 7A is a pictorial illustration of connector 70, showing both top and bottom views of the connector, as well as details of structures on the top side of the connector. FIG. 7B is a sectional illustration of connector 70 taken along a line VIIB-VIIB in FIG. 7A.

Connector 70, like connector 36, comprises dielectric substrate 42, which in this case has metal layers deposited on its top and bottom surfaces. There is no need in this embodiment, however, for any metal structures on the sides of the connector. Cable 34 typically comprises a ribbon cable, with wires 40 arrayed side-by-side with a known pitch. Typically, the cable comprises ten wires at a pitch of 100 μm, although a greater or smaller number of wires, as well as a finer or coarser pitch, may likewise be used. On the top surface of connector 70, an array of conducting traces 72 is printed with a pitch equal to the pitch of cable 34. Wires 40 are then attached to respective traces 72 simply by aligning cable 34 properly with the traces and soldering the wires to the traces. Suitable assembly methods for this purpose are known in the art.

Each trace 72 connects to a through-hole 74, which passes through substrate 42 to a corresponding conductive element 42 printed on the bottom surface of connector 70. Holes 74 are plated through in order to make electrical contact between each trace 72 and the corresponding element 42. Thus, soldering wires 40 to traces 72 connects the wires through to elements 42 simply and compactly. Connector 70 may then be installed in receptacle 60 (FIG. 5A) in the manner described above.

Although the embodiments described hereinabove relate specifically to flexible electronic imaging endoscopes, elements of these embodiments may also be applied, mutatis mutandis, in electronic instruments of other sorts. For example, the methods and devices described above may also be used in producing rigid endoscopes, as well as in both flexible and rigid borescopes for non-medical applications. Furthermore, the principles of the present invention may be applied, as well, in pre-assembling and testing electronic assemblies in elongate electronic probes of other sorts, in which a functional subassembly at the distal end must be connected by wires to a processing subassembly at the proximal end.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for assembling an endoscope that includes an imaging subassembly inside an insertion tube having distal and proximal ends, the method comprising:

coupling the imaging subassembly to a plurality of wires, which have respective first and second ends, by fixing the first ends of the wires to the imaging subassembly;

coupling a connector to the wires by fixing the second ends of the wires to the connector;

after coupling the imaging subassembly and the connector to the wires, installing the imaging subassembly in the insertion tube by passing the connector through the insertion tube from the distal end of the insertion tube to the proximal end; and after passing the connector through the insertion tube, inserting the connector in a receptacle.

2. The method according to claim 1, and comprising testing the imaging subassembly by receiving signals from the connector after coupling the imaging subassembly and the connector to the wires and before installing the imaging subassembly in the insertion tube.

3. The method according to claim 1, wherein inserting the connector in the receptacle comprises coupling the imaging subassembly to convey signals to a processing subassembly via the wires.

4. The method according to claim 1, wherein the connector has an axis and comprises a first array of conductive elements disposed along the axis, and wherein coupling the connector to the wires comprises connecting the wires to the conductive elements.

5. The method according to claim 4, wherein the receptacle comprises a second array of conductive pads, and wherein coupling the connector to the receptacle comprises aligning the first and second arrays, and exerting a pressure on at least one of the connector and the receptacle so as to engender an electrical contact between the conductive elements and the conductive pads.

6. The method according to claim 5, wherein coupling the connector to the receptacle comprises inserting between the first and second arrays an elastomeric material comprising alternating conductive and non-conductive layers so that the electrical contact is formed through the elastomeric material.

7. The method according to claim 4, wherein the connector comprises a dielectric substrate, and wherein the conductive elements are formed from a layer of conductive material that is disposed on the dielectric substrate.

8. The method according to claim 4, wherein while passing the connector through the insertion tube, the axis of the connector is approximately parallel to the wires.

* * * * *